United States Patent
Hayakawa et al.

(10) Patent No.: US 8,139,107 B2
(45) Date of Patent: Mar. 20, 2012

(54) DEFECT INSPECTION METHOD, DEFECT INSPECTION SYSTEM, AND COMPUTER READABLE STORAGE MEDIUM

(75) Inventors: Makoto Hayakawa, Koshi (JP); Hiroshi Tomita, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 1457 days.

(21) Appl. No.: 11/656,956

(22) Filed: Jan. 24, 2007

(65) Prior Publication Data

US 2007/0182814 A1 Aug. 9, 2007

(30) Foreign Application Priority Data

Feb. 8, 2006 (JP) .................................. 2006-31088

(51) Int. Cl.
*H04N 7/18* (2006.01)
(52) U.S. Cl. .......................................... 348/92; 348/87
(58) Field of Classification Search .................... 348/92, 348/87

See application file for complete search history.

(56) References Cited

U.S. PATENT DOCUMENTS

| 6,004,047 | A  | * | 12/1999 | Akimoto et al. | .............. | 396/604 |
| 6,411,377 | B1 | * | 6/2002  | Noguchi et al. | ............. | 356/237.4 |
| 7,652,276 | B2 | * | 1/2010  | Hayakawa et al.| ........ | 250/559.4 |
| 2005/0037272 | A1 | * | 2/2005 | Tanaka | ............................ | 430/30 |

FOREIGN PATENT DOCUMENTS

| JP | 5-107038   | 4/1993  |
| JP | 8-65000    | 3/1996  |
| JP | 10-247621  | 9/1998  |
| JP | 11-167210  | 6/1999  |
| JP | 2001-168010| 6/2001  |
| JP | 2002-267616| 9/2002  |
| JP | 2003-42972 | 2/2003  |
| JP | 2003-289030| 10/2003 |
| JP | 2004-173214| 6/2004  |
| JP | 2006-049630| 2/2006  |

* cited by examiner

*Primary Examiner* — Kristie Shingles
(74) *Attorney, Agent, or Firm* — Smith, Gambrell & Russell, LLP (57) ABSTRACT

In the present invention, an image of a substrate is picked up by an image pickup unit with the substrate being held by a transfer member. A drive unit for the transfer member is controlled by a driving signal from a first controller. A driving signal outputted to the first controller is outputted also to a second controller so that the second controller controls the image pickup unit based on the driving signal, thereby synchronizing drive of the transfer member with the image pickup by the image pickup unit. According to the present invention, the throughput in performing a defect inspection for the substrate is improved and a precise image is captured and subjected to accurate inspection.

14 Claims, 7 Drawing Sheets

DEFECT INSPECTION METHOD, DEFECT INSPECTION SYSTEM, AND COMPUTER READABLE STORAGE MEDIUM

BACKGROUND OF THE INVENTION

1. Field of the Invention

The present invention relates to a defect inspection method and a defect inspection system for a substrate and a computer readable storage medium.

2. Description of the Related Art

In a photolithography process in a manufacturing process of a semiconductor device, for example, a resist coating treatment for forming a resist film on a front surface of a substrate such as a wafer, exposure processing for exposure by irradiating a pattern on the front surface of the substrate, a developing treatment for developing the substrate after the exposure and so on are performed. The substrate for which a series of predetermined photolithography process is subjected to a so-called macro defect inspection by an inspection unit, such as whether or not a predetermined resist film is formed on the front surface of the substrate, or whether or not appropriate exposure processing is performed, and whether or not there is a scratch, or adherence of foreign substance.

The macro defect inspection is performed such that an image pickup unit, such as a CCD line sensor is moved relative to a mounting table mounting a substrate thereon to capture an image of the substrate and perform image processing on the image so as to determined presence or absence of a defect (Japanese Patent Application Laid-open No. 2002-267616). Further, in order to perform such a defect inspection in the series of photolithography process, it is also proposed to incorporate a defect inspection device for performing such a defect inspection in-line, for example, in a coating and developing treatment apparatus (Japanese Patent Application Lain-open No. 2001-168010).

However, provision of the above-described defect inspection device in the coating and developing treatment apparatus requires a space dedicated for the device and time accompanying transfer of the substrate into the dedicated defect inspection device and transfer-out after the inspection, resulting in reduced throughput.

SUMMARY OF THE INVENTION

Hence, the present inventors considered that an image pickup device is used to pick up an image of a substrate when the substrate is transferred by a transfer member so as to capture the image, but precise image data is required for use in the defect inspection, and such required precise image data cannot be obtained only by simply installing the image pickup device above a path for the transfer member. For example, when the transfer speed of the transfer member is greater than the image capture cycle of the image pickup device, the captured image shrinks in the transfer direction of the transfer member and, in contrast, when the speed is less than the cycle, the image expands in the transfer direction.

Therefore, an object of the present invention is to solve the above-described problems of throughput and space and to capture a precise image by picking up an image of a substrate by an image pickup unit with the substrate being held by a transfer member for transferring the substrate.

To achieve the above object, the present invention is a method of picking up an image of a substrate by an image pickup unit to inspect the substrate for a defect, wherein the image pickup is performed with the substrate being held and transferred by a transfer member for transferring the substrate, and wherein drive of the transfer member is synchronized with the image pickup by the image pickup unit when the image pickup unit picks up the image of the substrate.

By synchronizing dive of the transfer member with the image pickup by the image pickup unit as described above, a precise image can be obtained even if the image of the substrate is picked up by the image pickup unit while the substrate held by the transfer member is being transferred by the transfer member.

For the synchronization, image capture by the image pickup unit may be controlled based on a driving signal outputted from a controller to a drive unit for driving the transfer member.

Further, image capture by the image pickup unit may be controlled based on a feedback signal, for example, an encoder signal, outputted to a controller from a drive unit for driving the transfer member. Generally, when a transfer unit is moved by the drive unit, for example, a pulse motor, the encoder signal indicating that the transfer unit is moved from the drive unit side is outputted every second. Accordingly, the synchronization may be performed based on the feedback signal such as the encoder signal.

Other than the control of the image capture by the image pickup unit based on the driving signal used for the drive unit as described above, drive of the transfer member, for example, the driving speed may be controlled based on a control signal for controlling a timing of image capture by the image pickup unit. In this case, the image capture timing is preferably changed depending on a luminance on the substrate.

The defect inspection method as described above may be executed by a computer program installed in an appropriate controller such as a computer or the like, or recorded in a readable/writable storage medium, such as a hard disk, compact disk, flexible disk, magneto-optical disk, or the like.

As the system for implementing the above-described method, the following systems can be proposed.

Namely, according to another aspect of the present invention, the present invention is an inspection system for picking up an image of a substrate held by a transfer member for transferring the substrate to inspect the substrate for a defect, including: a drive unit for driving the transfer member; a first controller for controlling the drive unit; an image pickup unit for picking up an image of the substrate on the transfer member; and a second controller for controlling the image pickup unit. Further, a driving signal outputted from the first controller or outputted to the first controller in order to drive the drive unit is outputted also to the second controller so that the second controller controls the image pickup unit based on the driving signal.

According to still another aspect, the present invention is an inspection system for picking up an image of a substrate held by a transfer member for transferring the substrate to inspect the substrate for a defect, including: a drive unit for driving the transfer member; a first controller for controlling the drive unit; an image pickup unit for picking up an image of the substrate on the transfer member; and a second controller for controlling the image pickup unit. Further, an encoder signal outputted from the drive unit to the first controller is outputted also to the second controller from the first controller directly or via another controller so that the second controller controls the image pickup unit based on the encoder signal.

According to yet another aspect of the present invention, the present invention is an inspection system for picking up an image of a substrate held by a transfer member for transferring the substrate to inspect the substrate for a defect, including: a drive unit for driving the transfer member; a first controller for controlling the drive unit; an image pickup unit for picking up an image of the substrate on the transfer member; and a second controller for controlling the image pickup unit. Further, the second controller includes a reference clock for controlling a timing of image capture by the image pickup unit so that a driving signal is outputted to the first controller based on the reference clock. In this case, the second controller may further include a control unit for changing a cycle of the reference clock based on luminance information on the substrate being an image pickup object.

The image pickup unit is preferably placed above a path in which the substrate is transferred by the transfer member. Further, the image pickup unit may be provided at a transfer unit for supporting the transfer member.

According to the present invention, the image pickup is performed with the substrate being held by the transfer member for transferring the substrate, thereby improving the throughput as compared with the inspection by a dedicated inspection device as in the prior art and requiring no additional space for such an inspection device. Furthermore, it is possible to capture a precise image for inspection.

DETAILED DESCRIPTION OF THE INVENTION

Figure 1:
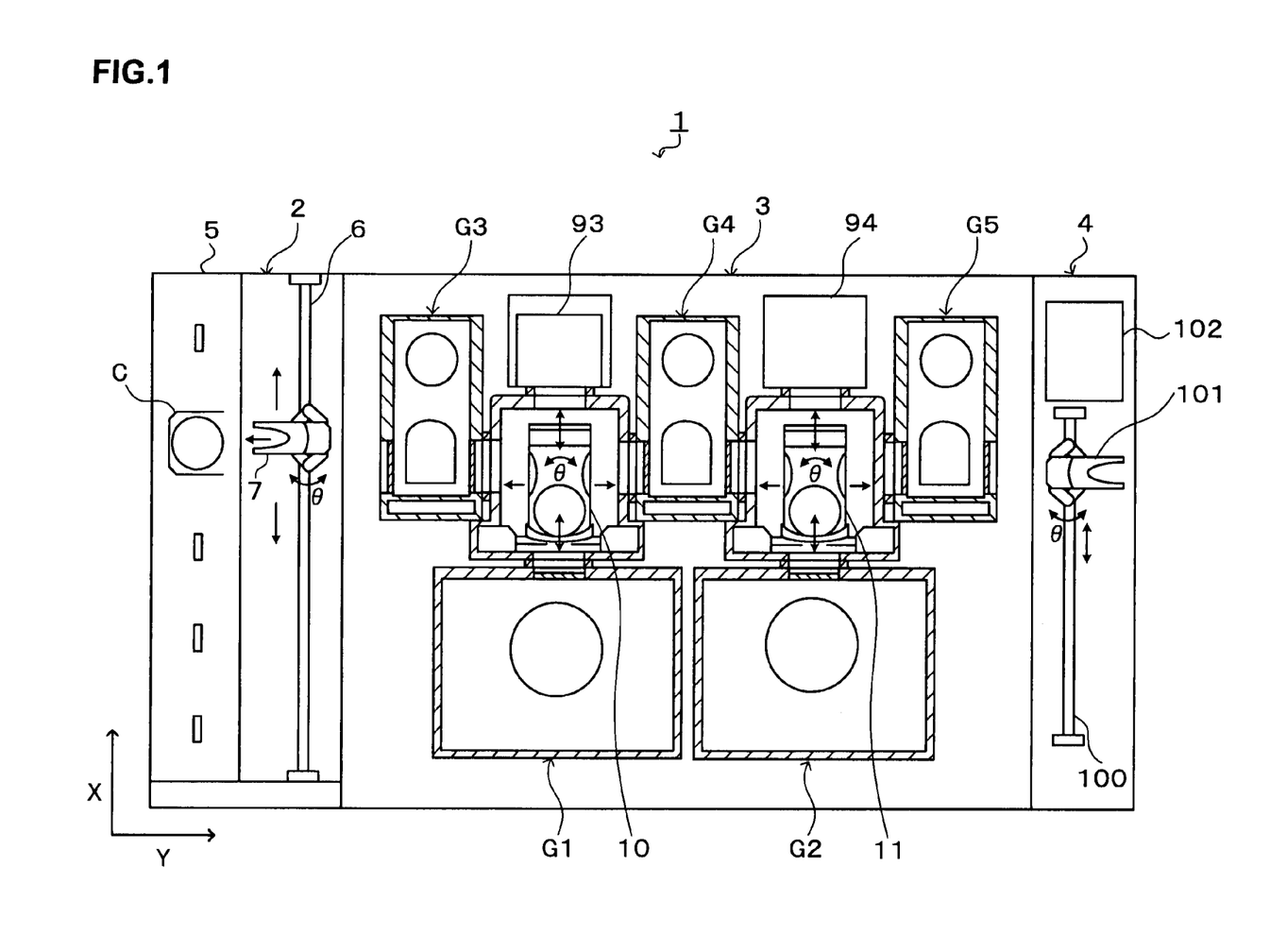
FIG. 1 is an explanatory view of the plane of a configuration of a coating and developing treatment apparatus including a defect inspection system according to an embodiment.
Figure 2:
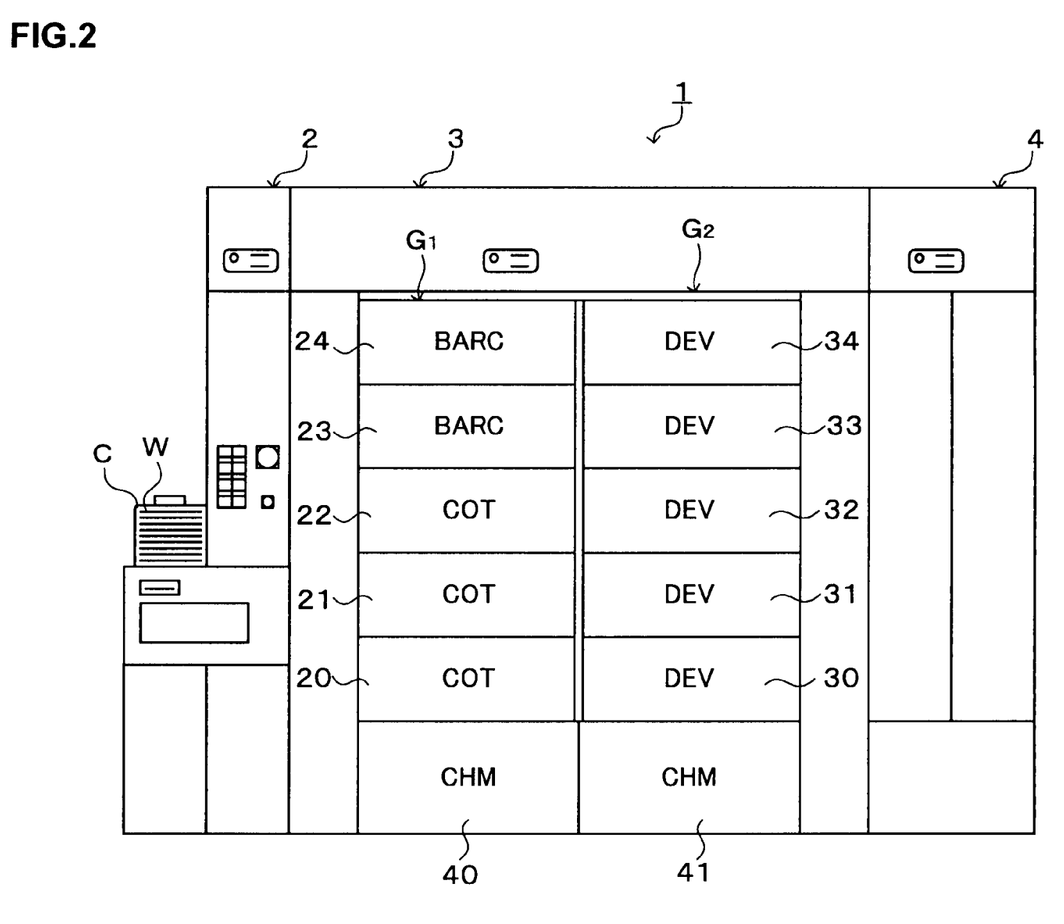
FIG. 2 is an explanatory view of the front of the coating and developing treatment apparatus in FIG. 1.
Figure 3:
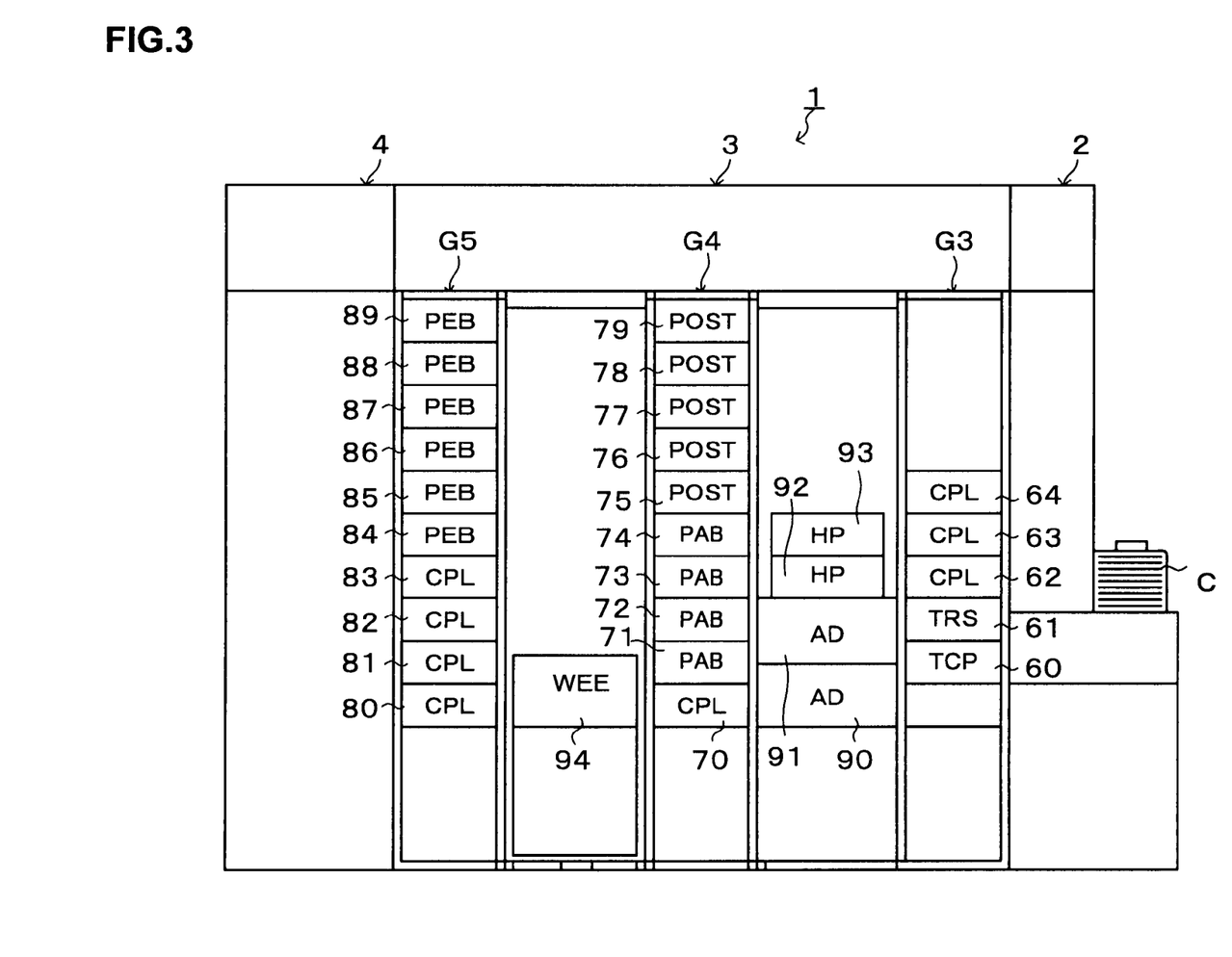
FIG. 3 is an explanatory view of the rear of the coating and developing treatment apparatus in FIG. 1.

Hereinafter, preferred embodiments of the present invention will be described. FIG. 1 is a plan view showing the outline of a configuration of a coating and developing treatment apparatus 1 in which a defect inspection system according to the present embodiment is incorporated, FIG. 2 is a front view of the coating and developing treatment apparatus 1, and FIG. 3 is a rear view of the coating and developing treatment apparatus 1.

The coating and developing treatment apparatus 1 has, as shown in FIG. 1, a configuration in which, for example, a cassette station 2 for transferring, for example, 25 wafers W per cassette as a unit from/to the outside into/from the coating and developing treatment apparatus 1 and transferring the wafers W into/out of a cassette C; a processing station 3 including a plurality of various kinds of processing and treatment units, which are multi-tiered, for performing predetermined processing or treatment in a manner of single wafer processing in a photolithography process; and an interface section 4 for passing the wafer W to/from an aligner (not shown) provided adjacent to the processing station 3, are integrally connected.

In the cassette station 2, a cassette mounting table 5 is provided and configured such that a plurality of cassettes C can be mounted on the cassette mounting table 5 in a line in an X-direction (a top-to-bottom direction in FIG. 1). In the cassette station 2, a wafer transfer body 7 is provided which is movable in the X-direction on a transfer path 6. The wafer transfer body 7 is also movable in a wafer-arrangement direction of the wafers W housed in the cassette C (a Z-direction; the vertical direction), and thus can selectively access the wafers W in each of the cassettes C arranged in the X-direction.

The wafer transfer body 7 is rotatable in a θ-direction around the Z-axis, and can access a temperature regulating unit 60 and a transition unit 61 for passing the wafer W which are included in a later-described third processing unit group G3 on the processing station 3 side.

The processing station 3 adjacent to the cassette station 2 includes, for example, five processing unit groups G1 to G5 in each of which a plurality of processing and treatment units are multi-tiered. On the side of the negative direction in the X-direction (the downward direction in FIG. 1) in the processing station 3, the first processing unit group G1 and the second processing unit group G2 are placed in order from the cassette station 2 side. On the side of the positive direction in the X-direction (the upward direction in FIG. 1) in the processing station 3, the third processing unit group G3, the fourth processing unit group G4, and the fifth processing unit group G5 are placed in order from the cassette station 2 side. Between the third processing unit group G3 and the fourth processing unit group G4, a first transfer unit 10 is provided. The first transfer unit 10 can selectively access the processing and treatment units in the first processing unit group G1, the third processing unit group G3, and the fourth processing unit group G4 and transfer the wafer W to them. Between the fourth processing unit group G4 and the fifth processing unit group G5, a second transfer unit 11 is provided. The second transfer unit 11 can selectively access the processing and treatment units in the second processing unit group G2, the fourth processing unit group G4, and the fifth processing unit group G5 and transfer the wafer W to them.

In the first processing unit group G1, as shown in FIG. 2, solution treatment units each for supplying a predetermined liquid to the wafer W to perform treatment, for example, resist coating units 20, 21, and 22 each for applying a resist solution to the wafer W, and bottom coating units 23 and 24 each for forming an anti-reflection film that prevents reflection of light at the time of exposure processing, are five-tiered in order from the bottom. In the second processing unit group G2, solution treatment units, for example, developing treatment units 30 to 34 each for supplying a developing solution to the wafer W to develop it are five-tiered in order from the bottom. Further, chemical chambers 40 and 41 each for supplying various kinds of treatment solutions to the solution treatment units in the processing unit groups G1 and G2 are provided on the lowermost tiers of the first processing unit group G1 and the second processing unit group G2, respectively.

As shown in FIG. 3, in the third processing unit group G3, for example, the temperature regulating unit 60, the transition unit 61, high-precision temperature regulating units 62 to 64 each for temperature-regulating the wafer W under temperature control with a high precision are five-tiered in order from the bottom.

In the fourth processing unit group G4, for example, a high-precision temperature regulating unit 70, pre-baking units 71 to 74 each for heating the wafer W coated with the resist solution, post-baking units 75 to 79 each for heat-processing the wafer W after developing treatment, are ten-tiered in order from the bottom.

In the fifth processing unit group G5, a plurality of thermal processing units each for performing thermal processing for the wafer W, for example, high-precision temperature regulating units 80 to 83, and a plurality of post-exposure baking units 84 to 89 each for heat-processing the wafer W after exposure, are ten-tiered in order from the bottom.

As shown in FIG. 1, a plurality of processing and treatment units are arranged on the positive direction side in the X-direction of the first transfer unit 10, for example, adhesion units 90 and 91 each for performing hydrophobic treatment on the wafer W and heating units 92 and 93 each for heating the wafer W being four-tiered in order from the bottom as shown in FIG. 3. As shown in FIG. 1, on the positive direction side in the X-direction of the second transfer unit 11, for example, an edge exposure unit 94 is disposed which selectively exposes only the edge portion of the wafer W to light.

In the interface section 4, for example, a wafer transfer body 101 moving on a transfer path 100 extending in the X-direction and a buffer cassette 102 are provided as shown in FIG. 1. The wafer transfer body 101 is movable in the Z-direction and also rotatable in the θ-direction and thus can access the not-shown aligner adjacent to the interface section 4, the buffer cassette 102, and the fifth processing unit group G5 and transfer the wafer W to them.

Figure 4:
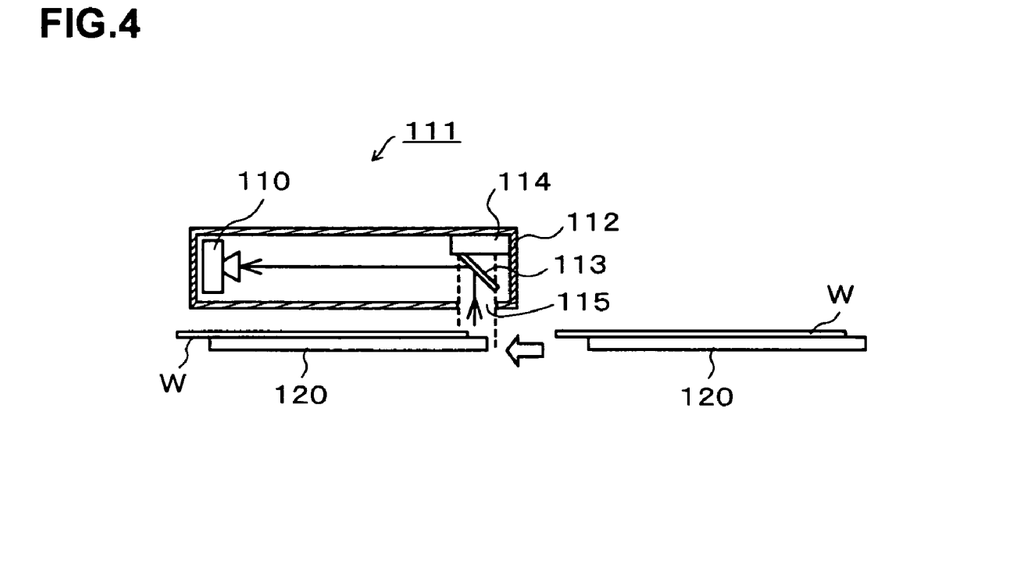
FIG. 4 is an explanatory view of the side of an image pickup unit used in the defect inspection system according to the embodiment.
Figure 5:
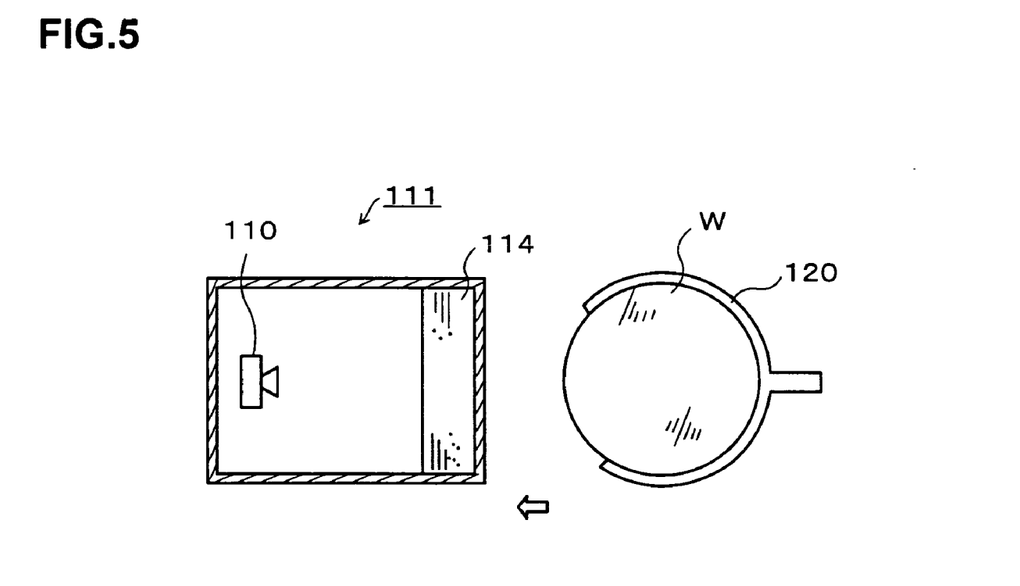
FIG. 5 is an explanatory view of the plane of the image pickup unit used in the defect inspection system according to the embodiment.

Next, the defect inspection system incorporated in the coating and developing treatment apparatus 1 configured as described above will be described. FIG. 4 shows a side section of an image pickup unit 111 incorporating an image pickup device 110 in the defect inspection system and FIG. 5 shows a plane section of the same, in which a CCD line sensor is used as the image pickup device 110 in this embodiment.

The image pickup device 110 is housed on one side in a casing 112 constituted of panels or the like. On the other end side in the casing 112, a half mirror 113 is provided. Behind the half mirror 113, an illumination device 114 is provided. An opening 115 is formed in a lower surface of the other end portion of the casing 112, so that illumination from the illumination device 114 passes through the half mirror and is applied from the opening 115 to below the image pickup unit 111. Accordingly, a reflected light off an object lying within the irradiation region is reflected by the half mirror 113 and captured into the image pickup device 110. In other words, the image pickup device 110 can pick up the image of the object lying within the irradiation region.

Figure 6:
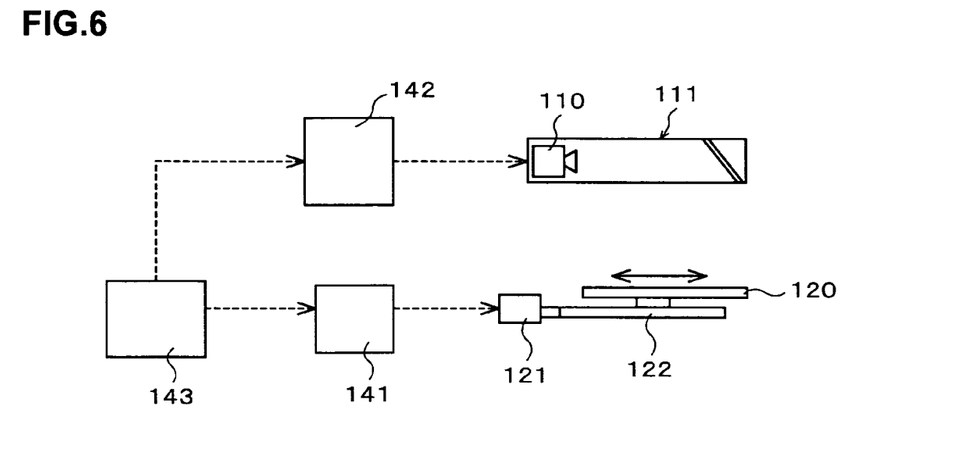
FIG. 6 is an explanatory view showing the outline of a configuration of the defect inspection system according to the embodiment.

According to the image pickup unit 111 having the above-described configuration, the image pickup device 110 can pick up an image by substantially scanning the entire upper surface of the wafer W while the wafer W held by a transfer member 120 incorporated in the previously described first transfer unit or second transfer unit 11 is being moved under the image pickup unit by the transfer member 120, for example, as shown in FIG. 6 showing the outline of the defect inspection system according to the embodiment.

In the defect inspection system according to this embodiment shown in FIG. 6, the above-described transfer member 120 is driven by a drive unit 121, for example, pulse motor or the like. More specifically, the transfer member 120 is movable along a base 122 in a direction with a reciprocal arrow in the drawing, and the movement is transmitted to the transfer member 120 via, for example, a timing belt (not shown) by drive of the drive unit 121.

Describing a control system of the defect inspection system according to this embodiment, as shown in FIG. 6, drive of the above-described drive unit 121, such as ON, OFF, speed and the like is controlled by a first controller 141. In other words, drive, stop, even speed of drive and so on of the drive unit 121 are controlled by a driving signal outputted from the first controller 141 to the drive unit 121. An encoder signal at that time is then outputted from the drive unit 121 driven by the driving signal to the first controller 141.

The image pickup device 110 is controlled by a second controller 142. In this embodiment, image pickup, an image pickup timing, an image capture time, and so on by the image pickup device 110 are controlled by an external synchronization signal outputted from the second controller 142 to the image pickup device 110. The picked-up image is then outputted to the second controller 142 and subjected to necessary image-processing in the second controller 142 or a third controller 143.

The first controller 141 and the second controller 142 are controlled by the higher third controller 143 which controls the whole coating and developing treatment apparatus 1. In other words, based on a driving signal outputted from the third controller 143 to the first controller 141, the first controller 141 outputs a predetermined driving signal to the drive unit 121. On the other hand, the third controller 143 outputs the driving signal also to the second controller 142 at the same timing as the driving signal outputted to the first controller 141, so that the second controller 142 outputs the external synchronization signal to the image pickup device 110 based on the driving signal. In this case, the relation between the driving signal and the external synchronization signal may be such that an image of one shot (one line) is picked up for one pulse of driving signal or an image of one shot (one line) is picked up for a plurality of pulses.

Figure 7:
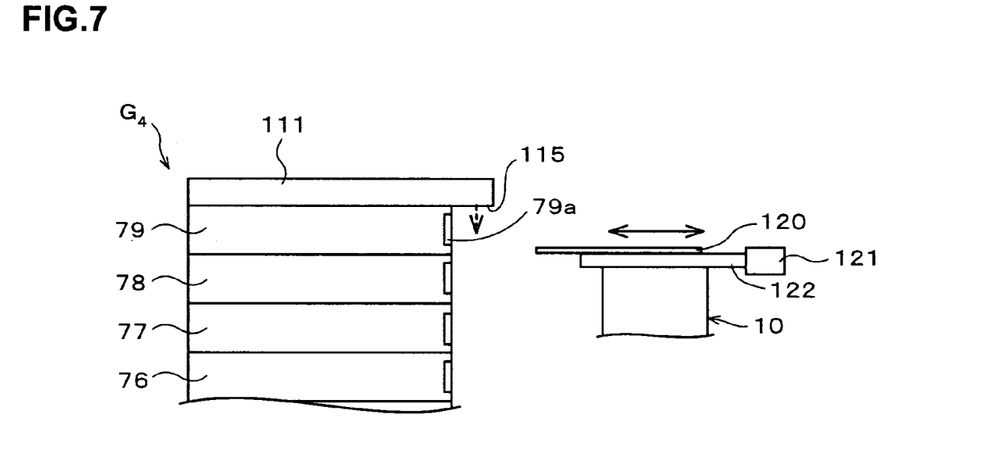
FIG. 7 is an explanatory view showing a placement example of the image pickup unit of the defect inspection system according to the embodiment.

The image pickup unit 111 is placed above a path in which the substrate is transferred by the transfer member 120. For example, as shown in FIG. 7, the image pickup unit 111 is placed on the post-baking unit 79 located on the uppermost tier in the fourth processing unit group G4. In this event, the image pickup unit 111 is placed such that the opening 115 in its lower surface is located directly above the front or rear of a transfer-in/out port 79a of the post-baking unit 79.

Figure 8:
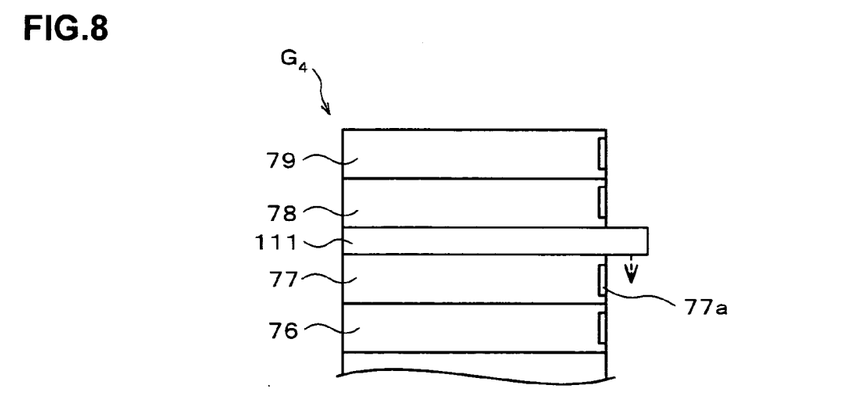
FIG. 8 is an explanatory view showing another placement example of the image pickup unit of the defect inspection system according to the embodiment.

The place where the image pickup unit 111 is placed is not limited to the above, but may be, for example, between the post-baking unit 78 on the second tier from the top and the post-baking unit 77 on the third tier from the top in the fourth processing unit group G4 as shown in FIG. 8. In that case, the image pickup unit 111 is placed such that the opening 115 in its lower surface is located directly above the front or rear of a transfer-in/out port 77a of the post-baking unit 77.

Note that the image pickup unit 111 may be placed, not limited on the processing unit in the fourth processing unit group G4, but on another processing or treatment unit in the other processing unit group G1, G2, G3, or G5.

The defect inspection system according to this embodiment has the above-described configuration, in which if the image pickup unit 111 is placed directly above, for example, the front of the transfer-in/out port 79a of the post-baking unit 79 as shown in FIG. 7, an image of the wafer W held by the transfer member 120 can be picked up when the wafer W is transferred into the post-baking unit 79 by the transfer member 120 or when the wafer W for which predetermined post-baking processing in the post-baking unit 79 has been finished is transferred out of the post-baking unit 79, so as to perform defect inspection for the wafer W.

In this case, to pick up the image of the wafer W, for example, when the wafer W is transferred into the post-baking unit 79 by the transfer member 120, the driving signal outputted from the third controller 143 is outputted to the second controller 142 at the time when driving the transfer member 120, based on which the external synchronization signal is outputted from the second controller 142 to the image pickup device 110, then based on which the image pickup device 110 picks up an image of the wafer W which is being held and transferred by the transfer member 120. Accordingly, the image pickup by the image pickup device 110 is synchronized with the movement of the transfer member 120. Accordingly, even if an image of the wafer W is picked up by the image pickup device 110 as described above while the wafer W held by the transfer member 120 is being transferred by the transfer member 120, a precise image can be obtained. In addition, an image of the wafer W can be picked up while it is being transferred by the transfer member 120 and the image can be captured and subjected to image processing required for defect inspection, thereby improving the throughput as compared with the inspection by a dedicated inspection device and requiring no space for such an inspection device.

Note that the control as described above is conducted following a computer program installed in the third controller 143, or recorded in various kinds of storage media readable in the third controller 143.

Figure 9:
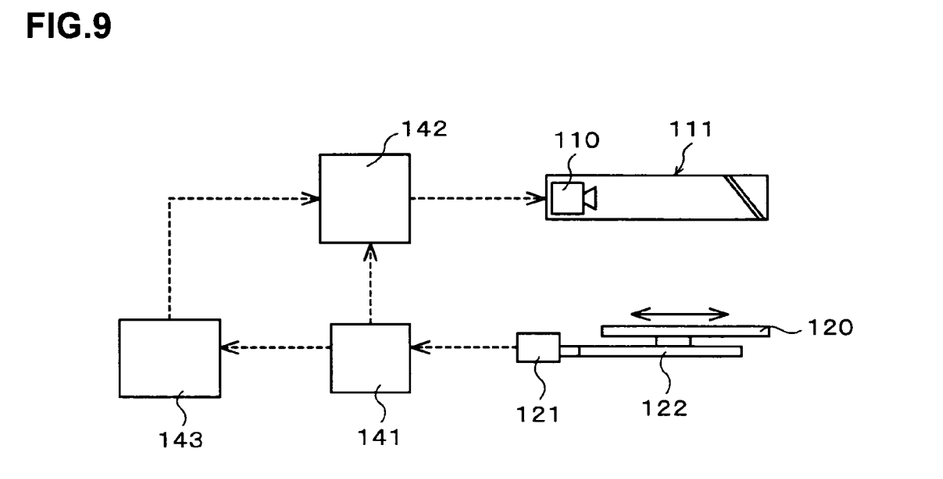
FIG. 9 is an explanatory view showing the outline of a configuration of the defect inspection system according to another embodiment.

Concurrently with the output of the driving signal to the first controller 141, the third controller 143 outputs the driving signal to the second controller 142, based on which the second controller 142 outputs the external synchronization signal to the image pickup device 110 in the above embodiment. In place of the configuration, for example, the encoder signal outputted from the drive unit 121 to the first controller 141 may be outputted directly to the second controller 142, or outputted to the second controller 142 via the third controller 143 as shown in FIG. 9, so that the second controller 142 outputs the external synchronization signal to the image pickup device 110 based on the encoder signal.

Figure 10:
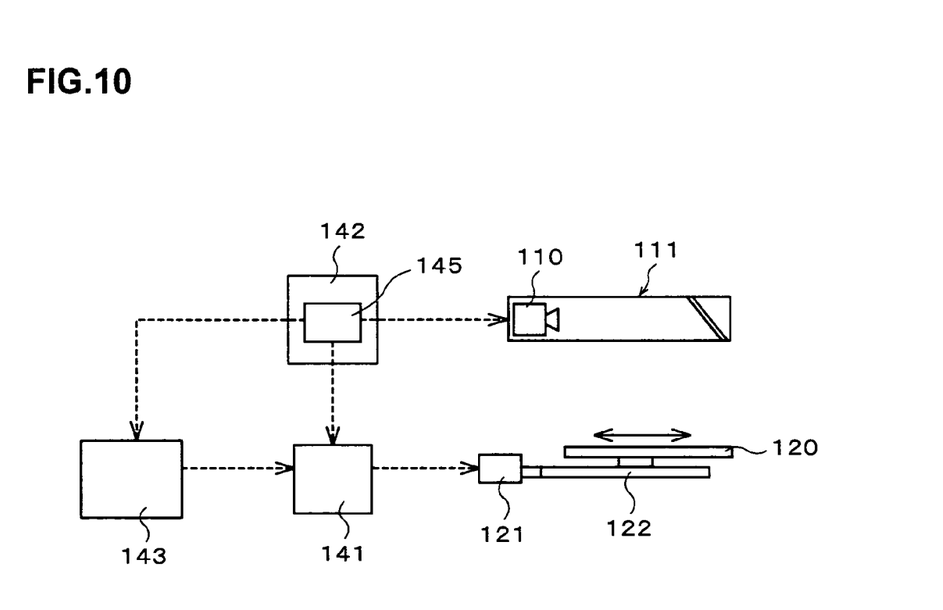
FIG. 10 is an explanatory view showing the outline of a configuration of the defect inspection system according to another embodiment.

Although the external synchronization signal is outputted to the image pickup device 110 based on the driving signal or a feedback signal on the drive unit 121 side in the above configuration, drive on the drive unit 121 side may be controlled based on the signal on the image pickup device 110 side. For example, if the second controller 142 has a reference clock 145 being a reference for outputting the external synchronization signal to the image pickup device 110 as shown in FIG. 10, image pickup by the image pickup device 110 can be synchronized with transfer (movement) of the wafer W by the transfer member 120 by directly outputting the driving signal based on the reference clock 145 to the first controller 141 or outputting the driving signal to the first controller 141 via the third controller 143. Note that the reference clock 145 may be provided in the image pickup device 110 or the third controller 143.

Incidentally, the luminance (brightness and darkness) on the wafer W may be different due to the difference in reflectivity of the front surface of the wafer W depending on the state of the wafer W to be inspected, and therefore when an image is picked up in the same image capture time for every case, the captured image is so-called overexposed or underexposed, failing to obtain an image with high precision. In this case, for example, the illuminance by the illumination device 114 may be changed depending on the brightness on the wafer W, but there is a case in which the illumination device cannot be changed as describe above, or a case in which the illumination device varies in conditions when the illuminance is changed to fail to, for example, collate, compare and so on with the reference wafer. In this case, the length of the image capture cycle will be changed. In such a case, according to the change, drive, such as the moving speed, by the drive unit 121 need to be changed as a matter of course.

Figure 11:
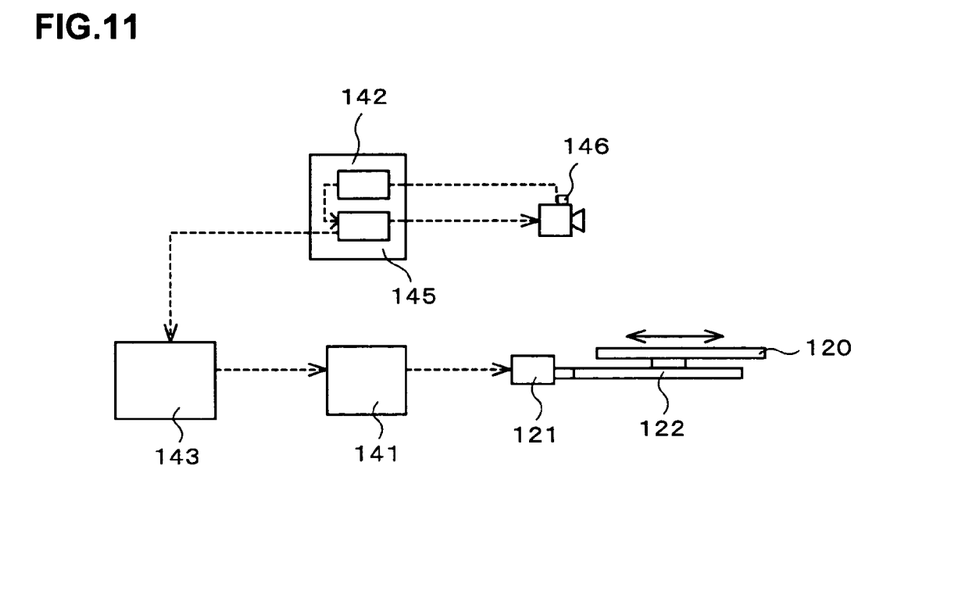
FIG. 11 is an explanatory view showing the outline of a configuration of the defect inspection system according to another embodiment.

The example shown in FIG. 11 shows a configuration to automatically control the length of the image capture cycle in such a case, in which a light quantity adjusting unit 147 is configured to output to the reference clock 145 a correction signal for correcting the image capture cycle based on a signal from a sensor 146 for measuring, for example, the reflectivity of the front surface on top of the wafer W so that the brightness of the image captured by the image pickup device 110 falls within a predetermined brightness range which has been previously set. This automatically corrects the length of the image capture cycle by the image pickup device 110, according to which the driving signal to the drive unit 121 is also controlled. Accordingly, even when images of the wafers W different in reflectivity are picked up, image pickup by the image pickup device 110 and drive of the transfer member 120 by the drive unit 121 can be synchronized to obtain precise images. Further, the defect inspection can be performed with the same reference even for a wafer W with a high reflectivity or a wafer W with a low reflectivity.

Incidentally, if the reflectivity of the front surface of the wafer being an inspection object has been previously known, it is not necessary to use the above-described sensor 146, and information about the wafer whose reflectivity has been known may be registered in the second controller 142, or a storage medium having such information recorded therein may be connected to the second controller 142 every inspection so that the information is read.

Figure 12:
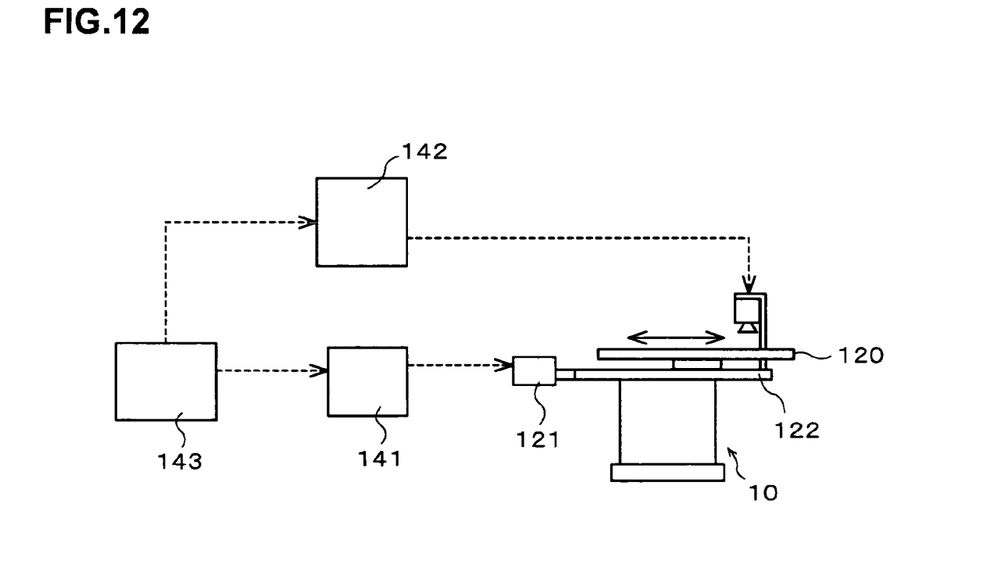
FIG. 12 is an explanatory view showing the outline of a configuration of the defect inspection system according to another embodiment in which an image pickup device is provided on a transfer unit side.

Although the image pickup device 110 is placed on a processing or treatment unit in the processing unit group G1, G2, G3, G4, or G5 in order to be placed above the path in which the wafer W is transferred in the above embodiment, the image pickup device 110 may be placed through use of an appropriate support member 150 on the base 122 in the first transfer unit 10 or the second transfer unit 11 as shown in FIG. 12 so that an image of the wafer W on the transfer member 120 is picked up. According to such a configuration, the image pickup unit 111 does not need to be placed on the processing or treatment unit, and an image of the wafer W can be picked up not only at the time when it is being transferred into/out of the processing or treatment unit but also at any position to perform inspection.

Each of the above-described inspection systems may further include a sensor for detecting the attitude of the substrate on the transfer member 120, an attitude controller for controlling the attitude of the image pickup device 110, and a control unit for controlling the attitude controller based on a substrate attitude signal from the sensor. Thus, even when the wafer W held by the transfer member 120 is inclined, for example, the image pickup device 110 can be controlled in attitude depending on the inclination to appropriately pick up the image of the wafer W.

Note that although the inspection object, that is, the substrate to be image-picked up by the image pickup device 110 is a semiconductor wafer in the above-described embodiments, the present invention is applicable, not limited to the above, but even to substrates, for example, for various kinds of flat displays as a matter of course.

Although the first controller 141, the second controller 142, and the third controller 143 are configured as discrete units in each of the above-described embodiments, it is only required to essentially provide a control unit substantially having a function of conducting the controls performed by the above controllers, and therefore it is not always necessary to embody the controllers as discrete units.

The present invention is useful for performing a surface inspection using an image of the substrate.

What is claimed is:

1. A method of picking up an image of a substrate being transferred between processing and treatment units in a coating and developing treatment apparatus by an image pickup unit to inspect the substrate for a defect, said method comprising:
   causing a transfer member, which is part of the treatment apparatus but removed from the image pickup unit, to hold and transfer the substrate between units of the treatment apparatus,
   synchronizing drive of the transfer member with the image pickup unit,
   obtaining, by the image pickup unit while the image pickup unit and the transfer member are synchronized, the image of the substrate, and
   inspecting the obtained image for a defect.

2. The method as set forth in claim 1, wherein image capture by the image pickup unit is controlled based on a driving signal outputted from a controller to a drive unit for driving the transfer member.

3. The method as set forth in claim 1, wherein image capture by the image pickup unit is controlled based on a feedback signal outputted to a controller from a drive unit for driving the transfer member.

4. The method as set forth in claim 1, wherein drive of the transfer member is controlled based on a control signal for controlling a timing of image capture by the image pickup unit.

5. The method as set forth in claim 4, wherein the image capture timing is changed depending on a luminance on the substrate.

6. An inspection system for picking up an image of a substrate that is transferred between processing and treatment units in a coating and developing treatment apparatus by a transfer member for transferring the substrate to inspect the substrate for a defect, said inspection system comprising:
   a drive unit for driving said transfer member; a first controller for controlling said drive unit;
   an image pickup unit for picking up an image of the substrate on said transfer member; and
   a second controller for controlling said image pickup unit,
   wherein a driving signal outputted from said first controller or outputted to said first controller in order to drive said drive unit is outputted also to said second controller so that driving of said transfer member to transfer the substrate and controlling of said image pickup unit to pick up the image of the substrate are synchronized as said second controller controls said image pickup unit based on the driving signal.

7. The inspection system as set forth in claim 6, wherein said image pickup unit is placed above a path in which the substrate is transferred by said transfer member.

8. The inspection system as set forth in claim 6, wherein said image pickup unit is provided at a transfer unit for supporting said transfer member.

9. An inspection system for picking up an image of a substrate that is transferred between processing and treatment units in a coating and developing treatment apparatus by a transfer member for transferring the substrate to inspect the substrate for a defect, said inspection system comprising:
   a drive unit for driving said transfer member;
   a first controller for controlling said drive unit;
   an image pickup unit for picking up an image of the substrate on said transfer member; and
   a second controller for controlling said image pickup unit,
   wherein a feedback signal outputted from said drive unit to said first controller is outputted also to said second controller from said first controller directly or via another controller so that driving of said transfer member to transfer the substrate and controlling of said image pickup unit to pick up the image of the substrate are synchronized as said second controller controls said image pickup unit based on the feedback signal.

10. An inspection system for picking up an image of a substrate that is transferred between processing and treatment units in a coating and developing treatment apparatus by a transfer member for transferring the substrate to inspect the substrate for a defect, said inspection system comprising:
    a drive unit for driving said transfer member;
    a first controller for controlling said drive unit;
    an image pickup unit for picking up an image of the substrate on said transfer member; and
    a second controller for controlling said image pickup unit,
    wherein said second controller includes a reference clock for controlling a timing of image capture by said image pickup unit by outputting a driving signal to said first controller, based on said reference clock, to synchronize drive of said transfer member with said image capture.

11. The inspection system as set forth in claim 10, further comprising:
    a control unit for changing a cycle of said reference clock based on luminance information on the substrate being an image pickup object.

12. The inspection system as set forth in claim 10, wherein said reference clock is provided in said image pickup unit or another controller.

13. A non-transitory computer readable storage medium storing a computer program for causing a computer to execute a method of picking up an image of a substrate transferred between processing and treatment units in a coating and developing treatment apparatus by an image pickup unit to inspect the substrate for a defect, said method comprising:
    causing a transfer member, which is part of the treatment apparatus but removed from the image pickup unit, to hold and transfer the substrate between units of the treatment apparatus,
    synchronizing drive of the transfer member with the image pickup unit,
    obtaining, by the image pickup unit while the image pickup unit and the transfer member are synchronized, the image of the substrate, and
    inspecting the obtained image for a defect.

14. A method of picking up and inspecting an image of a substrate present in a coating and developing treatment apparatus that includes processing units, treatment units, a transfer member for transferring the substrate between the processing units and the treatment units, a drive unit for driving the transfer member, an image pickup unit, and a control means, said method comprising:

causing the transfer member to hold the substrate, outputting, by the control means, a driving signal to both the drive unit and the image pickup unit whereby movement of the transfer member is synchronized with image pickup by the image pickup unit,     obtaining, by the image pickup unit while the image pickup unit and transfer member movement are synchronized, an image of the substrate, and     inspecting the obtained image for a defect.

\* \* \* \* \*